United States Patent [19]

Franz et al.

[11] Patent Number: 5,028,431
[45] Date of Patent: Jul. 2, 1991

[54] ARTICLE FOR THE DELIVERY TO ANIMAL TISSUE OF A PHARMACOLOGICALLY ACTIVE AGENT

[75] Inventors: Thomas J. Franz, Watchung; Kishore R. Shah, Bridgewater; Agis Kydonieus, Kendall Park, all of N.J.

[73] Assignee: Hercon Laboratories Corporation, New York, N.Y.

[21] Appl. No.: 406,811

[22] Filed: Sep. 13, 1989

Related U.S. Application Data

[63] Continuation of Ser. No. 114,063, Oct. 29, 1987, abandoned.

[51] Int. Cl.$^5$ ............................................. A61F 13/00
[52] U.S. Cl. ..................................... 424/449; 424/448
[58] Field of Search ..................... 424/449, 448, 445; 514/946, 947

[56] References Cited

U.S. PATENT DOCUMENTS

| | | | |
|---|---|---|---|
| 3,734,097 | 5/1973 | Zaffaroni | 424/448 |
| 4,145,409 | 3/1979 | Pasarela | 424/411 |
| 4,292,303 | 9/1981 | Keith et al. | 424/449 |
| 4,540,408 | 9/1985 | Lloyd | 604/289 |
| 4,666,441 | 5/1987 | Andriola et al. | 604/897 |
| 4,695,464 | 9/1987 | Alderman | 424/449 |
| 4,710,383 | 12/1987 | Dick | 424/449 |

FOREIGN PATENT DOCUMENTS

| | | |
|---|---|---|
| 1223818 | 7/1987 | Canada . |
| 1223819 | 7/1987 | Canada . |
| 0196769 | 10/1986 | European Pat. Off. . |
| 2588474 | 4/1987 | France . |
| 87/02891 | 5/1987 | PCT Int'l Appl. . |
| 05514 | 9/1987 | PCT Int'l Appl. . |
| 10058 | 12/1984 | South Africa . |

OTHER PUBLICATIONS

Leyden and Grove, "Transdermal Delivery Systems Cutaneous Toxicology", Chapter 7, Transdermal Delivery Drugs 1987, vol. 11, pp. 99–107, Abstract by Kyonieris et al., C. A. 107, No. 102491f.
Claim 1, 4,666,716.
Chemical Abstracts, 102:20944715, vol. 102, p. 364, 1985.
Chemical Abstracts, 87:63145t, vol. 87, p. 100, 1977.
Fisher, Contact Dermatitis, 3rd Ed., published by Lea & Febiger, 1986, p. 154.
"Leukotrienes and Other Lipoxygenase Products in the Pathogenesis and Therapy of Psoriasis and Other Dermatoses," Archives of Dermatology, vol. 119, Jul. 1983, pp. 541 to 547.
Moncada et al, "Prostaglandins, Prostacyclin, and Thromboxane A$_2$", The Pharmaceutical Basis of Therapeutics, (Chapter 28, 7th Ed. (Goodman and Gilman's), published by McMillen Publishing Co., 1985, pp. 668 to 673.
Lynch et al, "Skin Immunology: The Achilles Heel to Transdermal Drug Delivery", Journal of Controlled Release, vol. 6, (1987), pp. 39 to 50.

Primary Examiner—Thurman Page
Assistant Examiner—Leon R. Horne
Attorney, Agent, or Firm—Sughrue, Mion, Zinn, Macpeak & Seas

[57] ABSTRACT

Described is an article for the controlled release and delivery to animal tissue of a pharmacologically active agent with or without an excipient and/or enhances which may be a causative factor in the occurrence of non-allergic or allergic contact dermatitis comprising an anti-dermatitis substance.

10 Claims, 7 Drawing Sheets

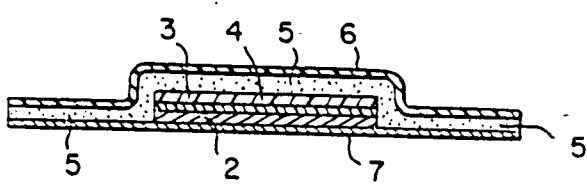
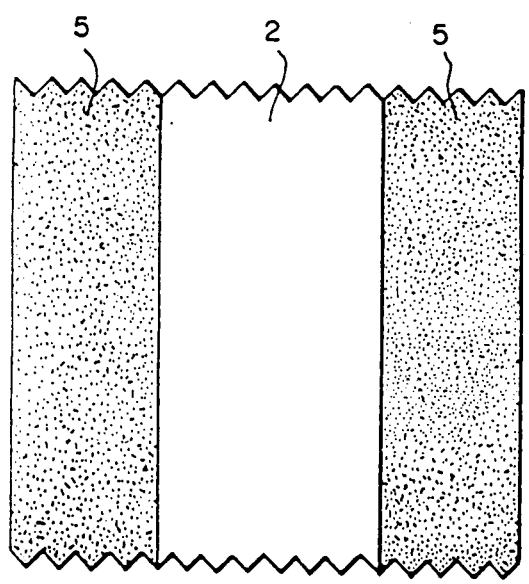
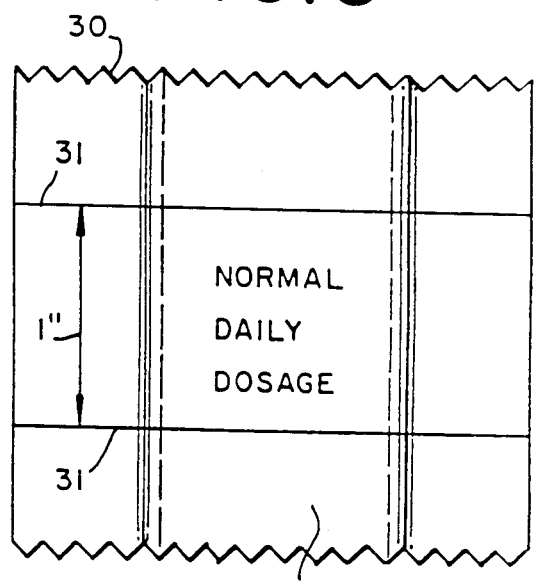
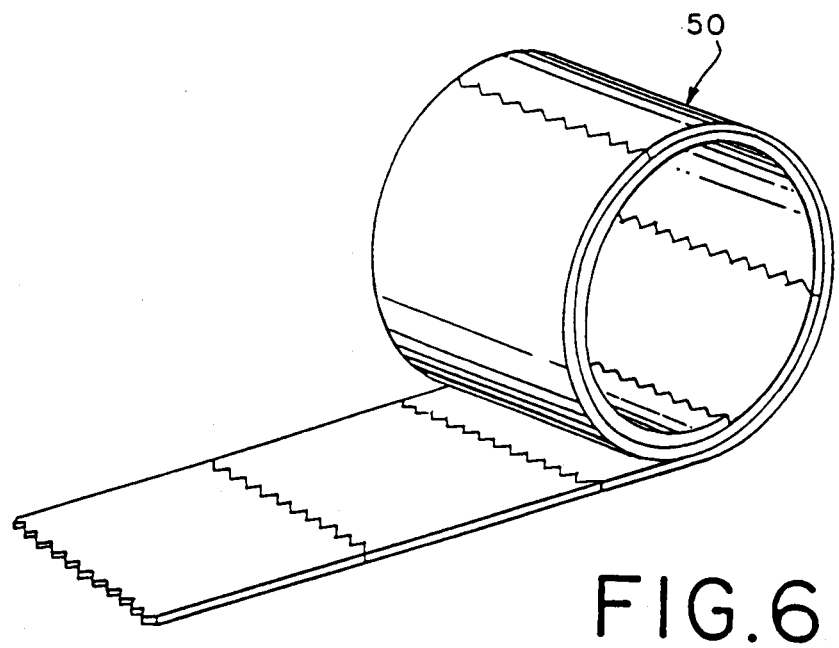

FIG.4
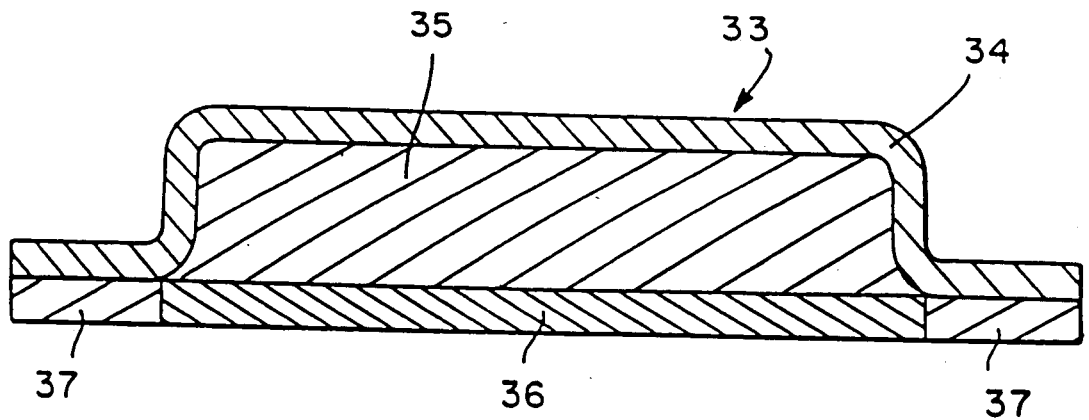
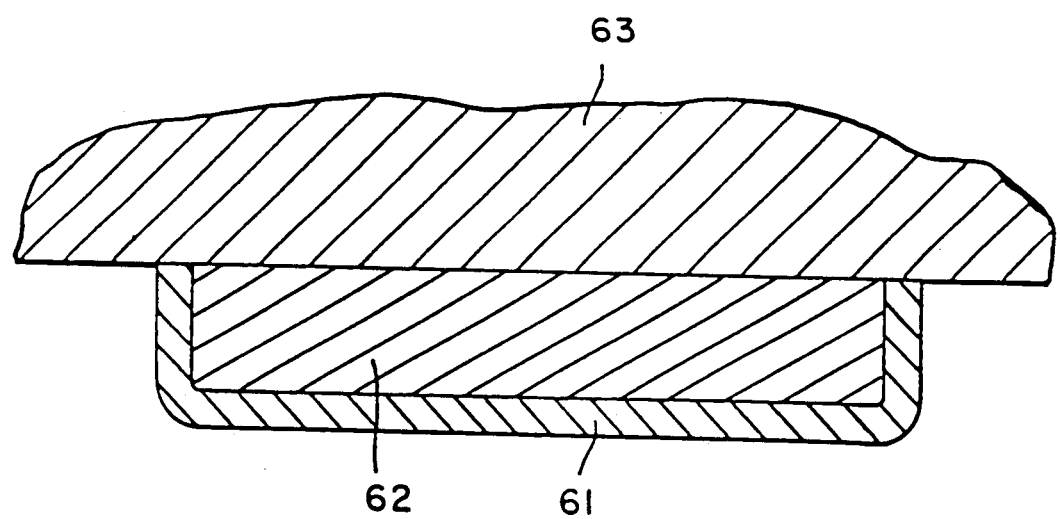
FIG.5

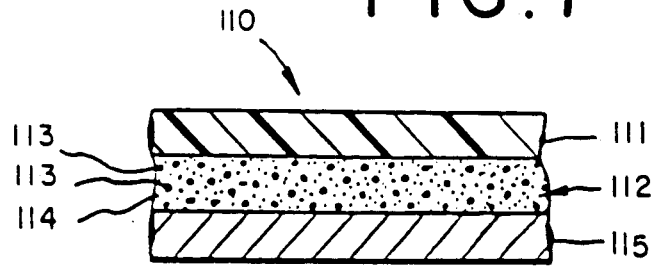
FIG. 7
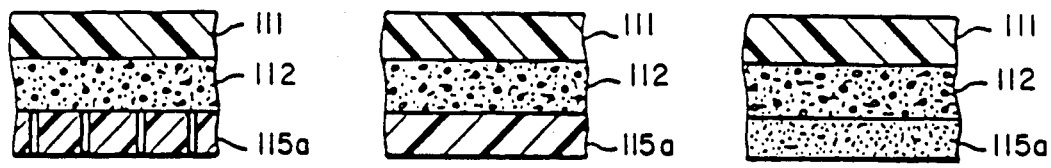
FIG. 7-A  FIG. 7-B  FIG. 7-C
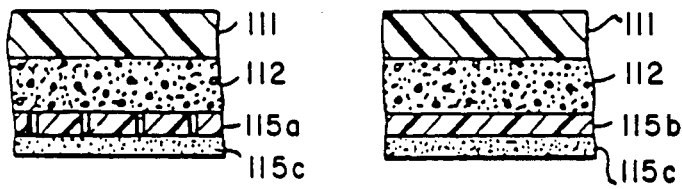
FIG. 7-D  FIG. 7-E
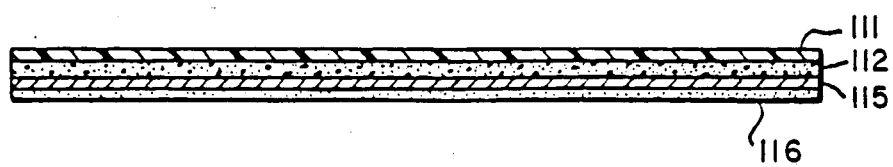
FIG. 8
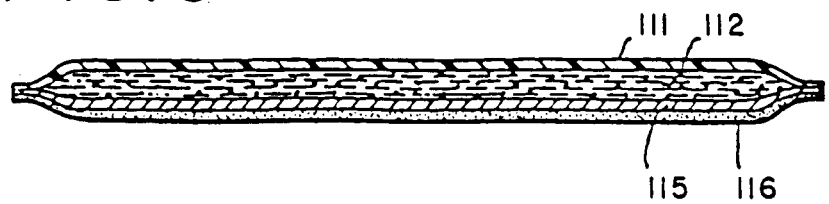
FIG. 9

ARTICLE FOR THE DELIVERY TO ANIMAL TISSUE OF A PHARMACOLOGICALLY ACTIVE AGENT

This is a continuation of application Ser. No. 07/114,063 filed Oct. 29, 1987 now abandoned.

BACKGROUND OF THE INVENTION

1. Field of the Invention

This invention relates broadly to articles of manufacture for administration of pharmacologically active substances, transdermally and by means of implant (e.g., subdermal implant). More specifically, this invention relates to articles for the controlled release and delivery to animal tissue (including but not limited to epidermal tissue) of a composition of matter comprising at least one pharmacologically active agent with or without one or more excipients therefor and/or one or more enhancers therefor at least one of said pharmacologically active agents, excipients therefor and enhancers therefor being a causative factor in the occurrence of non-allergic or allergic contact dermatitis comprising an anti-dermatitic substance having a chemical constituency different from that of the chemical constituency of any of said pharmacologically active agents, any of said excipients therefor, or any of said enhancers therefor.

The articles of our invention may be in the form of transdermal controlled release systems wherein the reservoir for the pharmacologically active agent is a solid polymer, or a transdermal delivery device wherein the pharmacologically agent is delivered from for example, a gel through a microporous membrane to the tissue to be treated, or the control release article may be a dispenser for delivering a pharmacologically active agent contained in a heat-responsive composition using an osmotically effective solute, through a passageway from the dispenser. The anti-dermatitic substance may be, for example:

(a) corticosteroids;
(b) chemicals that compete with the arachidonic acid biotransformation;
(c) inhibitor substances for the arachidonic acid cascade;
(d) free radical scavenger substances;
(e) Vitamin E;
(f) nordihydroguaiaretic acid;
(g) Vitamin D; or
(h) leukotriene receptor antagonists or combinations thereof. Pharmacologically active substances which are known to cause contact dermatitis are, for example, (a) guanfacine;
(b) (5Z, 13E, 15R, 16R)-16-fluoro-15-hydroxy-9-oxo-prosta-5-dienoic acid;
(c) fluphenazine; and
(d) clonidine.

2. The prior Art

Relatively intensive efforts are currently being expended in the pharmaceutical industry to provide for the delivery, in a controlled release manner, of pharmacologically active agents to the skin, and to mucous membranes of animals without the causation of allergic or non-allergic contact dermatitis and without the causation of subdermal inflammation of the tissues being treated by the pharmacologically active agent.

Thus, for example, U.S. Pat. No. 4,668,510 issued on May 26, 1987 and U.S. Pat. No. 4,576,818 provide iodophors which exhibit effective degerming of skin, and mucous membranes of animals and which provide broad spectrum microbiocidal action without toxicity or irritation. The prior art includes evidence of a great effort to provide controlled release formulations which provide anti-inflammatory and analgesic products to the skin.

Thus, Japan Kokai 85/122,291 published on Dec. 11, 1986 and abstracted at Chemical Abstracts, Vol. 106, No. 125909s discloses a transdermal tape containing diclofenac sodium as the active ingredient in an anti-inflammatory and analgesic transdermal tape having a soft pressure sensitive adhesive layer. The abstract state:

"An anti-inflammatory and analgesic transdermal tape contains diclofenac sodium and an organic acid such as citric acid. Diclofenac sodium is readily absorbed by the skin from this tape in the presence of the acid. Thus, 2-ethylhexyl acrylate 55, methoxyethyl acrylate 30, vinyl acetate 15, and azobisisobutyronitrile 0.3 parts by weight were mixed and heated at 60°-63° in 125 parts of ethyl acetate for ten hours and the polymer was cured for two hours at 80° C. Diclofenac sodium and citric acid were added in such a way that the concentrations in the formulation after drying were 20 and 4% by weight respectively. The mixture was applied to a removable liner to give a tape containing 400 micrograms diclofenac sodium per square centimeter."

South African Patent 8410-058 and German Offenlegungsschrift 33 47 278A published on June 24, 1985 disclose prolonged percutaneous release compositions containing an active substance, preferably by anti-inflammatory agent in an elastomer mixture consisting of diene rubbers. By the same token, South African Patent 8410-059 and German Offenlegungsschrift 33 47 277 published on Dec. 27, 1984 disclose prolonged percutaneous release compositions containing an active substance, preferably an anti-inflammatory agent in an elastomer mixture consisting of amorphous olefinic copolymers.

Canadian Letters Patent 1,223,818 issued on July 7, 1987 and 1,223,819 issued on July 7, 1987 disclose penetrating topical pharmaceutical compositions containing N-(2-hydroxyethyl)-pyrrolidone and 1-dodecyl-azacycloheptan-2-one. More specifically, Canadian Letters Patent 1,223,818 discloses and claims:

"A penetration-enhancing pharmaceutical composition for topical application comprising:
(a) about 0.01% to about 10%, by weight, of a non-steroidal anti-inflammatory agent selected from the group consisting of salicylic acid, acetyl salicylic acid, methyl salicylate, glycol salicylate, salicylmides, benzyl-2,5-diacetoxybenzoic acid, ibuproten, fulindac, naproxen, keto-profen, etofenamate, phenylbutazone, indomethacin, piroxican, and mixtures thereof;
(b) 0% to about 80% by weight of a solvent selected from ethanol and 2-propanol;
(c) 0% to about 80% by weight water;
(d) about 10% to about 99.9% by weight of a penetration-enhancing vehicle consisting essentially of:
 (i) N-(2-hydroxyethyl)pyrrolidone, and
 (ii) a cell-envelope disordering compound selected from the group consisting of methyl laurate, oleic acid, oleyl alcohol, monoolein, myristyl alcohol, and mixtures thereof;
wherein component (d)(i) and (d)(ii) are present in a ratio of (d)(i):(d)(ii) of about 5:1 to about 100:1 by weight."

More specifically, Canadian Letters Patent 1,223,819 discloses and claims:

"A penetration-enhancing pharmaceutical composition for topical application comprising:
 (a) about 0.01% to about 10%, by weight, of a non-steroidal anti-inflammatory agent selected from the group consisting of salicylic acid, acetyl salicylic acid, methyl salicylate, glycol salicylate, salicylmides, benzyl-2,5-diacetoxybenzoic acid, ibuprofen, fulindac, naproxen, keto-profen, etofenamate, phenylbutazone, indomethacin, piroxicam, and mixtures thereof;
 (b) 0% to about 80% by weight of a solvent selected from ethanol and 2-propanol;
 (c) 0% to about 80% by weight water;
 (d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)azacyclopentan-2-one, and mixtures thereof; and
 (e) about 1.0% to about 35% by weight of 1-dodecylazacycloheptan-2-one."

Bonney, et al, Arzneim.-Forsch, 35(4), pages 715–720 (abstracted at Chemical Abstracts, Vol. 103, No. 81418h) discloses the use of 2-(3-(1,1-dimethylethyl)-5-methoxy phenyloxazolo (4,5-b)pyridine as a topical anti-inflammatory and analgesic compound lacking systemic activity and gastric side effects. It is indicated that this compound is as potent as indomethacin in inhibiting ultra-violet light-induced erythema in guinea pig skin and it is further indicated that this compound is an effective analgesic when applied topically to the rat footpad. It is further indicated that the compound is a cyclooxygenase inhibitor and an inhibitor of prostaglandin E2 but not leukotriene C4 synthesis.

Tsukada, et al, Arzneim.-Forsch, 28(3), pages 428≧438 discloses the anti-inflammatory, analgesic, anti-pyretic and other pharmacological effects of osepinao-(6,11-dihydro-11-oxodibenz(b,e)oxepin-3-acetic acid and compared the effects with know non-steroidal anti-inflammatory drugs such as indomethacin.

SUMMARY OF THE INVENTION

It is an object of the present invention to provide an article of manufacture for the controlled release and delivery to animal tissue (including but not limited to animal epidermal tissue) of a composition of matter comprising at least one pharmacologically active agent with or without one or more excipients therefor and/or enhancers therefor, at least one of said pharmacologically active agents, excipients therefor or enhancers therefor being a causative factor in the occurrence of non-allergic or allergic contact dermatitis comprising an anti-dermatitic substance. The invention is differentiated from the prior art in that the chemical constituency of any of the pharmacologically active agents, or any of the excipients therefor, or any of the enhancers therefor are different from the chemical constituency of the anti-dermatitic agent or agents used in conjunction therewith in the practice of our invention.

Thus, our invention is to be differentiated from inventions drawn to combinations of anti-inflammatory drugs, such as that disclosed in PCT Patent 87/02891 entitled "Compounds and method for the Topical Treatment of Inflammation and Pain" which is drawn to:

"Esters of methyl salicylate with certain non-steroidal anti-inflammatory drugs (NSAID's) can be used for topical administration to mammals, to elicit a response which combines the anti-inflammatory and analgesic effects of the NSAID and the counter-irritant effect of the methyl salicylate. Typical NSAID's which can be used in this way are aspirin (acetylsalicic acid), ibuprofen and indomethacin. Advantageously, the NSAID-methyl salicylate ester is administered in the form of a pharmaceutical composition, such as an ointment, gel, lotion, cream or the like."

Broadly, the article of our invention includes the use of anti-dermatitic substances which may be one or combinations of the following groups:
 (a) corticosteroids;
 (b) chemicals that compete with the arachiodonic acid biotransformation;
 (c) inhibitor substances of the arachiodonic acid cascade;
 (d) free radical scavenger substances;
 (e) Vitamin E;
 (f) nordihydroguaiaretic acid;
 (g) Vitamin D; and
 (h) leukotriene receptor antagonists.

More specifically, our invention is based on the solutions of problems directly associated with the fact that many drugs irritate the skin when used in, for example, transdermal drug delivery systems. Such irritation results in epidermal and dermal inflammation which persists beyond the time that the patch is removed from the skin and may be symptomatic to the patient.

With reference to that aspect of our invention concerning the use of corticosteroids to prevent skin irritation associated with transdermal drug delivery, it is well known that corticosteroids are a class of drugs used for their anti-inflammatory activity. One aspect of our invention concerns the coadministration of a corticosteroid with another drug from a transdermal patch. The coadministration of a suitably potent corticosteroid at a constant rate blocks the inflammatory response normally caused by the other drug being delivered. A mildly irritating "other" drug only requires the use of a weak corticosteroid whereas a strong irritant requires the use of a corticosteroid of high potency. Coadministration of the corticosteroid from the patch with the "other" drug is essential since the anti-inflammatory activity needs to be maintained at a constant level to offset the constant delivery rate of the irritating "other" drug.

Examples of corticosteroids useful in the practice of our invention are set forth at pages 18 and 19 of Canadian Letters Patent 1,223,819 incorporated by reference herein and include (but are not limited to) alpha-methyldexamethasone, beta, methyl-betamethasone, beclomethasone dipropionate, betamethasone benzoate, betamethasone dipropionate, betamethasone valerate, clobetasol valerate, desonide, desoxymethasone, dexamethasone, diflorasone diacetate, difluocortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its ester, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, hydroxyltriamcinolone and beclomethasone dipropionate.

The amount of corticosteroid useful in the practice of our invention, particularly when used with transdermal patches either in the gel example or in the polymer example vary from about 0.5% up to about 3% by weight of the weight of the article being utilized for supplying to the animal tissue the pharmacologically active agent (different from the corticosteroid).

With reference to that aspect of our invention concerning the use of inhibitors of the arachidonic acid cascade to prevent contact dermatitis associated with, for example, transdermal delivery, it has been determined that products of the arachidonic acid cascade are important from a pathophysiologic standpoint in a number of skin diseases in which inflammation is a prominent part. We have further determined that drugs which inhibit key enzymes in the process (e.g., phospholipase $A_2$, 5-lipoxygenase, 12-lipoxygenase, or cyclo-oxygenase) or block the end-organ response (e.g., receptor antagonists) are effective in the treatment of inflammatory skin diseases.

As a result of the application of our invention, it is now possible to prevent the occurrence of contact dermatitis, both irritant or allergic, through the coadministration of one or more selective inhibitors of the arachiodonic acid cascade. By preventing even the possibility of contact dermatitis, certain drugs which have been considered unsuitable for transdermal application because of this adverse reaction have now become useable.

With reference to that aspect of our invention concerning the use of free-radical scavengers for eliminating or minimizing irritation and/or sensitization of skin associated with, for example, transdermal delivery of some drugs, it is now recognized that the irritation mechanism involves inflammatory reaction of skin caused by the products of arachidonic acid transformations in the epidermis and whole skin. Arachidonic acid is released as a result of physical, chemical or hormonal stimulation. The transformation of arachidonic acid to its metabolic products (leukotrienes, 12-hydroxyeicosatetraenoic acid, and prostaglandins) which are responsible for the inflammatory reaction, is an enzyme (lipoxygenase and cyclo-osygenase) catalyzed free-radical oxidative process.

An aspect of our invention thus concerns the incorporation of one or more free-radical scavengers in the formulation of, for example, a transdermal patch for a drug known to cause skin sensitization or irritation. Upon application of the patch to the skin, the free-radical scavenger will be delivered to the skin along with the drug by a process of diffusion. The free-radical chemical transformations of arachidonic acid to inflammatory metabolites are entirely prevented or effectively minimized by the presence in the skin of free-radical scavengers.

Some of the free-radical scavengers operable in the practice of our invention include hindered phenols such as 2,6-ditertiarybutyl-para-cresol (BHT), p-tertiarybutyl catechol, hydroquinone, benzoquinone, and N,N-diethylhydroxyamine.

With reference to that aspect of our invention concerning the use of combinations of corticosteroids and arachidonic acid cascade inhibitors to prevent irritation and sensitization associated with, for example, transdermal delivery of "other" drugs, contact dermatitis has been found to be caused as a result of application to the skin in transdermal devices of many drugs having an irritant or allergic effect. Since both the development and expression of these reactions are complex and involve many cellular and biochemical reactions as well as mediators, blockade of these adverse reactions requires the use of more than one anti-dermatitic agent.

We have found it appropriate to use anti-dermatitic agents that have different mechanisms of action and affect different steps in the inflammatory cascade, e.g., membrane stabilization and lipoxygenase inhibition, or receptor blockade. Thus, a combination of a corticosteroid (as exemplified supra) and one or more inhibitors of the arachidonic acid cascade, when incorporated into, for example, a transdermal device containing an irritant "other" drug, will block the adverse reactions caused by the irritant or sensitizing "other" drug. Coadministration of the two or more anti-dermatitic agents from the patch with the irritant or sensitizing "other" drug is essential since the anti-inflammatory activity needs to be maintained at a constant level to offset the constant delivery rate of the irritant "other" drug.

We have further determined that materials similar to arachidonic acid which would be biotransformable in similar ways to arachidonic acid compete with the arachidonic acid biotransformation and, therefore, less arachidonic acid will be transformed into products that would be irritating, such as leukotrienes and prostaglandins with four double bonds. It has further been determined that the products of the biotransformation of the chemicals of similar nature to arachidonic acid are not irritating due to the different number of double bonds or the presence of triple bonds. Such chemicals include eicosatetraynoic acid, eicosapentanoic acid and dihomolinoleic acid. We have found that other chemicals of similar chemical structure as the aforementioned three chemicals are also useful. Thus, for example, these chemicals could be delivered from the same patch as the drug causing the irritation or they can be given orally in larger amounts or in a combination thereof. The above mentioned chemicals which compete with the arachidonic biotransformation have been found to be useful in conjunction with chemicals that inhibit the steps of the arachidonic biotransformation cascade such as antioxidants, steroids and receptor antagonists.

We have further determined that irritation and sensitization caused by the specific drug applied to the skin will be minimized or eliminated by pretreatment and/or addition of the following ingredients in, for example, a transdermal delivery patch containing the drug that causes the irritation. These ingredients applied alone or in combination include, Vitamin D, nordihydroguaiaretic acid and/or Vitamin E.

As will be seen from the examples set forth in the "Detailed Description of the Drawings" section, infra, the anti-dermatitic agent which will substantially inhibit or eliminate non-allergic or allergic contact dermatitis as a result of treatment of animal tissue with a pharmacologically active agent with or without one or more excipients therefor and/or one or more enhancers therefor may be added from the same article as the pharmacologically active agent and, indeed, may be admixed with such pharmacologically active agent; or the anti-dermatitic agent may be applied to the animal tissue from a source apart from the source from which the pharmacologically active agent is applied. Thus, for example, the anti-dermatitic agent may be applied from the same drug reservoir as the pharmacologically active agent is applied from; or the anti-dermatitic agent may be applied from a reservoir separate from the reservoir containing the pharmacologically active agent.

Our invention contemplates, specifically, articles for the controlled release and delivery to animal tissues, preferably animal epidermal tissues, of one or more pharmacologically active agents with or without one or more excipients therfor and/or one or more enhancers therefor which agents, excipients and/or enhancers are also causative factors in the occurrence of non-allergic or allergic contact dermatitis. Such as article comprises:
(a) a polymer layer (for example, a polyvinyl chloride-polyvinyl acetate layer);
(b) one or more pharmacologically active agents with or without one or more excipients therefor or one or more enhancers therefor, at least one of which is a causative factor in the occurrence of non-allergic or allergic contact dermatitis and each of which is chemically compatible with said polymer, in intimate admixture with said polymer; and
(c) at least one anti-dermatitic substance chemically compatible with (i) one or more of said pharmacologically active agents, one or more excipients therefor and one or more enhancers therefor; and (ii) said polymer and said anti-dermatitic substance being in intimate admixture with said polymer and-/or one or more of said pharmacologically active agents, one or more excipients therefor and/or one or more enhancers therefor.

Said anti-dermatitic substance having a chemical constituency different from that of the chemical constituency of any of of said pharmacologically active agents or any of said excipients therefor or any of said enhancers therefor, whereby when a surface of said polymer layer is in contact with the animal epidermal tissue to be treated with one or more of the pharmacologically active substances, one or more of said pharmacologically active substances, excipients therefor and/or enhancers therefor is absorbed into and through said animal epidermal tissue and thence into the circulatory system of said animal, one or more of said pharmacologically active substances, excipients therefor and/or enhancers therefor being present in such a concentration in said polymer layer then an effective amount of one or more of said pharmacologically active substances, excipients therefor and/or enhancers therefor is absorbed into said animal in a prescribed period of time without any occurrence during or after said period of time of non-allergic or allergic contact dermatitis capable of being caused by one or more of said pharmacologically active agents, excipients therefor and/or enhancers therefor, said anti-dermatitic substance being in such a concentration in said polymer as to prevent the occurrence of said non-allergic or allergic contact dermatitis.

Examples of irritating enhancers against which the anti-dermatitic agents of our invention are active are as follows:
oleic acid;
oleyl alcohol;
linoleic acid;
propylene glycol;
hexylene glycol;
mirataine BB (having the structure:

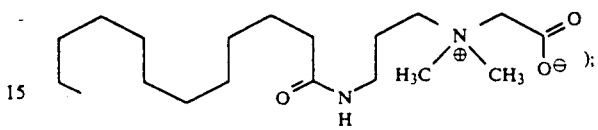

dimethyl sulfoxide;
dimethyl formamide;
dimethyl acetamide;
decyl methyl sulfoxide;
N-methyl pyrrolidone;
ethanol;
isopropyl alcohol; and
t-butanol.

The anti-dermatitic agent may be applied simultaneously with the application of the "other" drug or "other" pharmacologically active agent or the anti-dermatitic agent may be applied during a period of time proximate to that point in time that the pharmacologically active agent is being applied. Thus, as a general range of time, the anti-dermatitic agent may be applied from 12 hours prior to application of the "other" drug up until about 12 hours subsequent to the application of the "other" drug.

The anti-dermatitic agent useful in the practice of our invention may be employed in one or more of the components of any of the transdermal devices disclosed in the following publications, which publications are incorporated by reference herein:
Canadian Letters Patent 930,668;
U.S. Pat. No. 3,921,636 issued on Nov. 25, 1975;
Application for European Letters Patent 186,071 filed on Dec. 13, 1985;
U.S. Pat. No. 4,661,105 issued on Apr. 28, 1987;
U.S. Pat. No. 4,681,584 issued on July 21, 1987; and
U.S. Pat. No. 4,684,524 issued on Aug. 4, 1987.

Examples of excipients which are known to be causative agents of contact or allergic dermatitis and against which the anti-dermatitic agents of our invention are useful are as follows:
plasticizers such as dioctyl phthalate and diamyl adipate;
drug release control substances, such as polycaprolactone and cellulose acetate butyrate;
tethermixotropic active agent compositions to enhance the stability and the dispersibility of compositions, for example, surfactants including nonionic surfactants, such as sorbitan monostearate, polysorbate 80 (polyoxyethylene (20) sorbitan monooleate), and polyoxyethylene-4-stearate;
antioxidants to prevent degradation during prolonged periods of storage including 2,6-ditertiary butyl-p-cresol; propyl gallate, 6-ethoxy-1,2-dihydro-2,2,4-trimethylquinoline.

BRIEF DESCRIPTION OF THE DRAWINGS

FIG. 1 is a cross-sectional view of a preferred pharmacologically active agent/anti-dermatitic agent delivery device useful in accordance with the practice of our invention.

FIG. 2 is a plan view of a strip of material in accordance with our invention containing pharmacologically active agents and anti-dermatitic agents viewed from the surface which is applied to the patient's skin.

FIG. 3 is a plan view of material in accordance with this invention containing pharmacologically active agents and anti-dermatitic agents viewed from the surface away from the surface which is applied to the patient's skin.

FIG. 4 is an enlarged sectional schematic view of a specific embodiment of a device useful in the practice of our invention containing pharmacologically active agents and anti-dermatitic agents; a transdermal device for controlled release of a pharmacologically active agent simultaneously with controlled release of an anti-dermatitic agent from a plastisol monolayer through a membrane transdermally.

FIG. 5 is an enlarged sectional schematic view of another embodiment of the invention where there is no membrane separating the plastisol monolayer from the epidermis and whereby pharmacologically active agent is transported from the plastisol transdermally into the patient simultaneously with the transport of anti-dermatitic agent.

FIG. 6 is a perspective view of a roll of material in accordance with this invention containing both pharmacologically active agent and anti-dermatitic agent having a chemical constituency different from the chemical constituency of the pharmacologically active agent.

FIG. 7 is a fragmentary enlarged cross-sectional view depicting the essential component elements of a transdermal delivery system of a transdermal patch containing pharmacologically active agent and an anti-dermatitic agent having a chemical constituency different from the pharmacologically active agent.

FIGS. 7A, 7B, 7C, 7D and 7E are fragmentary enlarged cross-sectional view of several embodiments of component elements of a transdermal delivery system containing pharmacologically active agent and anti-dermatitic agent, with the chemical constituency of the pharmacologically active agent being different from the chemical constituency of the anti-dermatitic agent.

FIG. 8 is a cross-sectional view illustrating an embodiment of a transdermal patch containing pharmacologically active agent and anti-dermatitic agent, the chemical constituency of the anti-dermatitic agent being different from the chemical constituency of the pharmacologically active agent.

FIG. 9 is a cross-sectional view illustrating another embodiment of a transdermal patch containing pharmacologically active agent and anti-dermatitic agent, the chemical constituency of the anti-dermatitic agent being different from the chemical constituency of the pharmacologically active agent.

DETAILED DESCRIPTION OF THE DRAWINGS

Figure 10A:
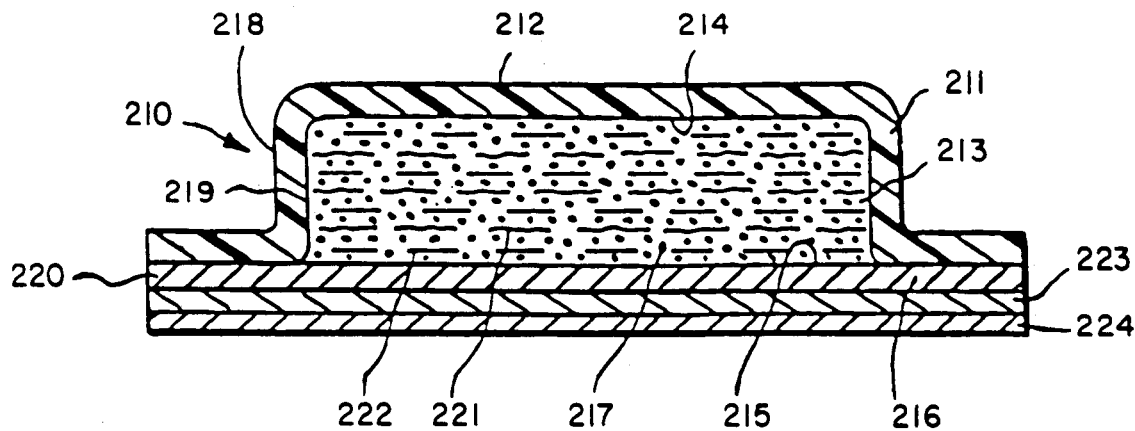
FIG. 10A is a medical bandage seen in open structure with the bandage defining a means for placing the bandage on the patient, the bandage containing a pharmacologically active agent and an anti-dermatitic agent, the chemical constituency of the pharmacologically active agent being different from the chemical constituency of the anti-dermatitic agent.

Referring to FIG. 1, the device 1 includes a solid plastisol monolayer 2 which is composed of or comprises resin, plasticizer, a pharmacologically active agent as set forth supra and an anti-dermatitic agent.

A formulation for layer 2 may comprise from about 2 up to about 70% by weight of the vinyl resin, from about 20 up to about 70% by weight of plasticizer composition, from about 0.5 up to about 35% by weight of pharmacologically active agent and the remainder being other excipients, such as materials which will enhance skin penetration, for example, AZONE ® having the structure:

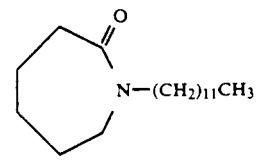

which happens to act both as a plasticizer and as an agent which enhances transdermal penetration of pharmacologically active agents, such as clonidine having the structure:

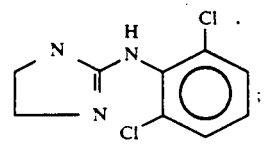

or RO 22-1327 having the structure:

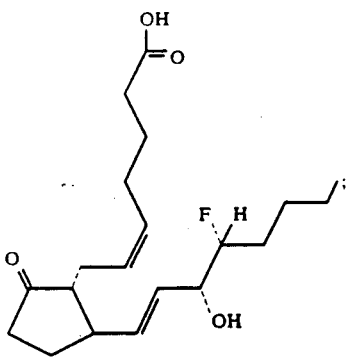

or guanfacine hydrochloride having the structure:

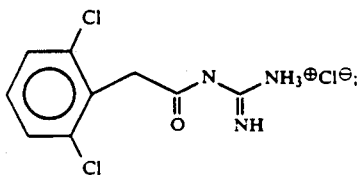

or fluphenazine having the structure:

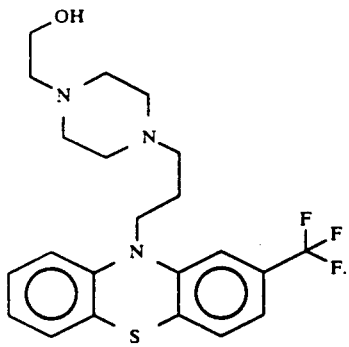

The articles of the present invention include but are not limited to transdermal devices and comprise, for example, a polyvinyl chloride plastisol layer in a fused state and a pharmacologically active agent uniformly dispersed in the fused layer which may be referred to as a reservoir for the pharmacologically active agent. An anti-dermatitic agent may be admixed with the pharmacologically active agent or anti-dermatitic agent may be in a layer separate from the pharmacologically active agent. When using polyvinyl chloride, the polyvinyl chloride reservoir may be prepared from polyvinyl chloride resin and a primary plasticizer for the resin.

When using polyvinyl chloride, the polyvinyl chloride resin employed in the practice of the present invention is that which is specifically used in preparing PVC plastisols, namely PVC resins which are made by the well known emulsion polymerization process, which are hard spheres of particle size between 0.05 and 20 microns, such as between 1 and 20 microns, for example, between 1 and 5 microns or between 0.05 and 1 micron, and which do not have the ability to absorb plasticizers to any great extent. Instead, the plasticizer wets the resin particles at room temperature and only then very slowly penetrates and solvates the resin. These PVC resins when mixed with plasticizers, such as a mixture of 30% primary plasticizer, 70% PVC resin, give a flowable liquid known as plastisol which can then be fused at, for example, approximately 250° F. for approximately 30 seconds to provide a solid polymer layer. The PVC resin employed in the present invention is in contrast to the general purpose PVC resins which are produced by suspension or bulk polymerization and which are used in calendering and extrusion processes, which are 50 to 200 microns, such as 100 to 150 microns in diameter, and are like sponges. Thus, the general purpose resins are capable of absorbing large amounts of plasticizers so that even a 50% DOP and 50% PVC resin would result in a non-flowing solid material. The molecular weight of the PVC resins employed in the present invention preferably is a weight average molecular weight between 80,000 and 250,000, such as a weight average molecular weight of 123,000. A suitable polyvinyl chloride resin is one sold by Occidental Chemical Co. under the designation FPC 6338 containing about 96% vinyl chloride monomer units of about 4% vinyl acetate monomer units. Thus, the polyvinyl chloride resin can be a copolymer containing preferably at least 90% by weight vinyl chloride monomer units, such as a copolymer based on vinyl chloride and vinyl acetate.

The polyvinyl chloride resin generally is present in the layer in an amount of 10 to 75 weight percent, preferably 20 to 70 weight percent, based on the total weight of the vinyl plastisol composition.

The primary plasticizer which is employed in the present invention can be dioctylphthalate (DOP), benzylbutylphthalate, tri-2-ethylhexylmalaete, dioctyl adipate, epoxidized soybean oil, polymeric adipate plasticizers, which are polymers of adipic acid with a monomer, such as propylene glycol, and for example can be obtained under the designation Drapex 334F from Witco Chemical Corp., or any other known primary plasticizer for PVC which is biologically acceptable.

The other examples of polyester adipates, glutarates and sebacates are:
polyester adipate P-644;
polyester glutarate P-530;
polyester glutarate P-540;
polyester glutarate P-550;
polyester glutarate P-7035;
polyester glutarate P-7035M;
polyester glutarate P-7046;
polyester glutarate P-7092; and
polyester glutarate P-1070
manufactured by the C.P. Hall Co., 7300 S. Central Avenue, Chicago, Illinois 60638. Other preferred plasticizers are those which are known as "adipate" plasticizers, for example, ADMEX ® which is a high molecular weight (MW=8000) adipate plasticizer manufactured by the Sherex Division of Nuodex Inc. In general, polyester plasticizers which are polyesters of (i) 1,4-terephthalic acid and/or 1,2-phthalic acid with (ii) ethylene glycol or 1,3-propylene glycol having molecular weights in the range of 4000–10,000 are preferred.

Another preferred plasticizer which also acts as a skin penetrating enhancer for pharmacologically active drugs which are intended for transdermal delivery from devices such as those set forth in FIGS. 1, 5 and 6 is the compound having the structure:

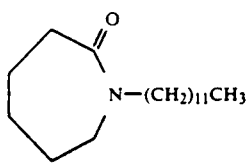

known as AZONE ® by the Nelson Research and Development Co.

Mixtures of known plasticizers can be used. The term "primary plasticizer" as used herein refers to a plasticizer which can be used alone to effect plasticization and is highly compatible with PVC at high concentrations, such as, for example, 150 parts per hundred. Primary plasticizers are contrasted with "secondary plasticizers" which, because of limited compatibility with PVC, cannot be used alone. See, Kirk-Othmer Encyclopedia of Chemical Technology, Volume 23, 3rd Edition, especially pages 913 and 914 for a discussion of primary and secondary plasticizers, which is incorporated by reference herein.

The primary plasticizer generally is present in an amount of 20 to 85 weight percent, preferably 20 to 70% based on the total weight of the vinyl plastisol layer.

The amount of pharmacologically active agent present in the PVC plastisol may range from about 0.5% by weight up to about 40% by weight. In addition, anti-dermititic agent may be present in the PVC plastisol layer in an amount ranging from about 0.1% by weight up to about 10% by weight.

The PVC plastisol may optionally contain other additives or "excipients" useful in the practice of this invention, for example, material which enhance skin penetrated of the pharmacologically active substances (e.g., 1,6-hexanediol and n-decyloleate) and thickeners, e.g., silica (preferably "fumed" silica, for example, AEROSIL ® in an amount of from 1-6% of the layer).

With reference to FIG. 1, the blended plastisol containing, for example, PVC, DOP, fluphenazine and fluocinonide is then coated at a rate of about 36 ounces-/yd$^2$ on a backing and then fused into solid plastisol layer 2. The backing may be a single layer of drug impermeable plastic or other material, but is preferably composed of two layers 3 and 4. Layer 3 may be MYLAR ® (polyester produced from ethylene glycol and phthalic anydride) about 0.5 mils thick, and layer 4 may be PVC, about 4 mils thick. The backing 3, 4 substantially blocks loss of drug and anti-dermatitic agent from the plastisol layer 2 other than in the direction of the surface which, in use, will contact the patient's skin.

The blended plastisol which is coated on the backing can be fused into a homogeneous solid by heating it for a short period, such as 15 to 30 seconds, at a temperature of, for example, 250° to 280° F. The use of a plastisol to form solid layer 2 enables layer 2 to be formed by using a low temperature for a short period of time, and provides conditions which do not affect the stability of the pharmacologically active agents.

A strip of solid plastisol layer 2 and backing 3,4 is then bonded to a pressure-sensitive adhesive layer 5 which in turn is provided with a non-adhesive backing 6 such as one made of plastic, moisture-proof fabric, aluminum foil, etc.

When not in use, the entire surface intended for skin contact is preferably covered with a release paper 7 or the like which is removed to expose surfaces of the adhesive layer 5 and drug containing plastisol layer 2 for application to the patient's skin.

FIG. 2 shows a plan view of the strip of material 20 during the stage of manufacture at which a strip of plastisol 2 (backing 3,4 not shown) has been applied to the adhesive tape (backing 6 not shown). For the preferred device for the controlled administration of pharmacologically active agent, e.g., drug RO 22-1327 having the structure:

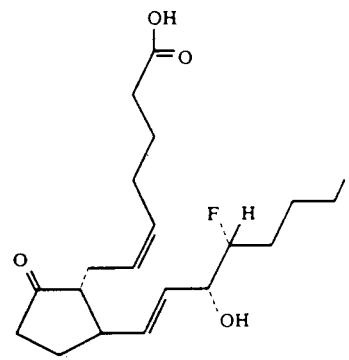

taken further together with anti-dermatitic agent fluocinonide having the structure:

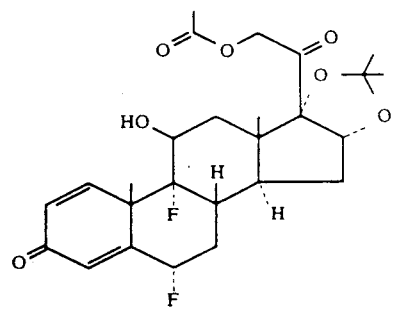

a plastisol strip preferably about one inch (1") in width is applied on a two and one-half inch (2½"), wide pressure-sensitive adhesive strip.

FIG. 3 shows a plan view of a strip of the material 30 in accordance with our invention; spaced lines 31 may be embossed or printed on the surface away from skin contact so that the patient may conveniently measure out and cut off the proper amount of the tape device to provide the prescribed daily dosage. For a device for administering the pharmacologically active agent, e.g., drug RO 22-1327 having the structure:

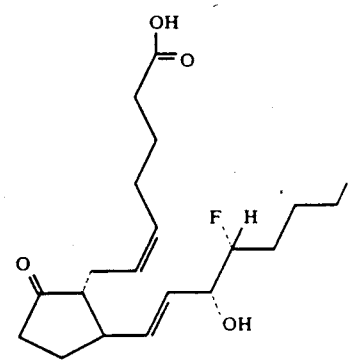

for example, a segment 1" long cut from the longer tape (resulting in an approximately one square inch (1 sq. in.) of active surface against the patient's skin) will provide a dosage of about 17 mg/24 hours (along with the anti-dermatitic drug, e.g., fluocinonide having the structure:

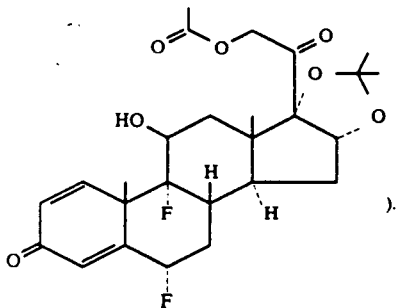

).

Referring to FIG. 4, the components of embodiment 33 are backing layer 34, a reservoir layer 35 that contains supplies of percutaneous absorption enhancer, pharmacologically active substance, such as fluphenazine having the structure:

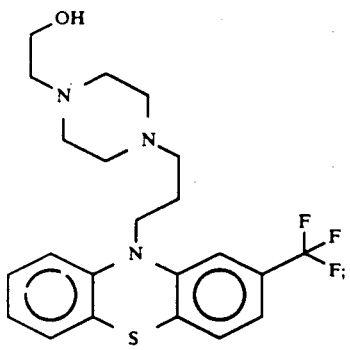

anti-dermatitic agent, fluocinonide having the structure:

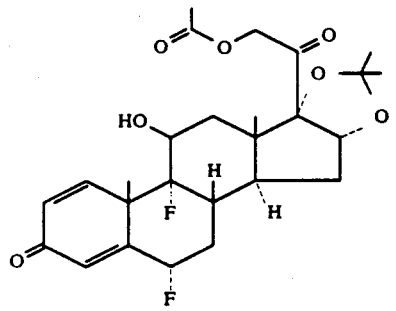

a diffusion membrane layer 36 and a peripheral ring 37 of contact adhesive. The diffusion membrane layer may be composed of a polymer, such as a copolymer of ethylene and methyl acrylate with the methyl acrylate being in the range of 2-90% by weight of the polymer, or blends of such copolymer with low density polyethylene, high density polyethylene or linear low density polyethylene. The contact adhesive component of embodiment 33 is in the form of a peripheral ring. Optionally, backing layer 34 may also be a semi-permeable membrane. Neither the pharmacologically active agent, the anti-dermatitic agent nor the enhancer passes through ring 37 and is therefore need not be permeable to those compositions. Optionally, the contact adhesive may be attached directly to the membrane 36 in which case the adhesive is selected so that it is permeable to the pharmacologically active agent and, in addition, to the anti-dermatitic agent.

Secondly, the base surface from which the pharmacologically active substance, the anti-dermatitic agent and the enhancer (e.g., AZONE®) is transferred to the skin is defined by diffusion membrane layer 36. The backing layer is not flat but, instead, forms a pocket or cavity in which the reservoir layer is held. The outer edge of the backing layer is sealed to the peripheral ring of the contact adhesive as more specifically set forth in U.S. Pat. No. 4,379,454 issued on Apr. 12, 1983, the disclosure of which is incorporated herein by reference. Similarly, an article within the contemplation of our invention may have a matrix as is illustrated in FIG. 5 wherein the backing 61 totally surrounds the PVC-plastisol-plasticizer matrix 62 and is firmly in place as with an adhesive on the skin 63. The anti-dermatitic agent may also be included in the adhesive.

As shown in FIG. 6, the device of the invention may conveniently be provided in the form of a tape roll 50 from which daily dosage requirements of the pharmacologically active agent along with the anti-dermatitic agent may be clipped by the patient.

The device is capable of application to humans or other animals capable of usefully absorbing pharmacologically active agents through the skin.

Other embodiments of our invention similar to those set forth in FIGS. 1-6, supra, are those useful in, for example, U.S. Pat. Nos. 4,573,996 and 4,573,995 issued on Mar. 4, 1986, the specifications for which are incorporated by reference herein.

Referring to FIGS. 7, 7A, 7B, 7C, 7D, 7E, 8 and 9, there is shown a transdermal delivery system 110 which comprises an impermeable backing member 111, a drug reservoir member 112 consisting of a pharmacologically active agent in admixture with anti-dermatitic agent 113 dispersed in carrier 114 and a rate controlling member 115, said system which together with a means to attach the system to the skin forms a transdermal patch or bandage. The rate controlling member may be (a) a microporous membrane 115a as seen in FIG. 7A, (b) a diffusion controlling membrane 115b as seen in FIG. 7B, (c) a rate controlling adhesive as seen in FIG. 7C (which also may contain anti-dermatitic agent or which may contain anti-dermatitic agent as an alternative to the reservoir containing the anti-dermatitic agent), (d) a combination of a microporous membrane 115a and an adhesive layer having rate controlling properties 115c which together perform the rate controlling function as seen in FIG. 7D, or (e) may be a combination of a diffusion controlling membrane 115b and a rate controlling adhesive layer 115c as seen in FIG. 7E.

When an adhesive is contributing to or performing a rate controlling function, the adhesive in these instances is performing a dual function of rate control and of attaching the transdermal delivery system to the skin. The adhesive as stated supra may also contain anti-dermatitic agent which diffuses to the skin simultaneously with the diffusion of the pharmacologically active agent.

FIG. 8 depicts an embodiment of a transdermal patch with attachment means 116 in which the drug reservoir is a solid with the drug reservoir also including the anti-dermatitic agent.

FIG. 9 depicts an embodiment in which the drug reservoir is a semi-solid or ointment wherein the face of the backing member contiguous to the drug reservoir is joined at the edges to the face of the microporous membrane contiguous to the drug reservoir. The drug reservoir contains in addition to pharmacologically active agent, anti-dermatitic agent. The edges are joined preferably by heat-sealing but also may be sealed by crimping, using sealants and by other means for effecting a seal.

The impermeable backing member 111 is preferably of a polyester occlusive film. Other materials suitable for a backing include foil, polyethylene coated foil, polyethylene, Mylar polyester, polypropylene and polyvinyl chloride.

The drug/anti-dermatitic agent reservoir is a dispersion of the pharmacologically active agent such as clonidine having the structure:

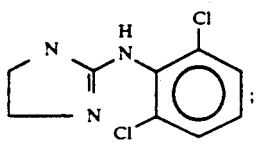

anti-dermatitic agents, such as fluocinonide having the structure:

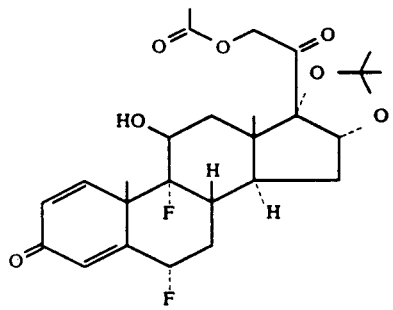

in a carrier.

The carrier may be a solid, i.e., of a non-mobile or non-flowable material or may be of a semi-solid preparation often referred to as ointments. Suitable semi-solid carriers include gelled mineral oil, e.g., mineral oil gelled with 5% polyethylene (commercially available as Plexi Gel 50W from Parke Davis), polyisobutylene, aluminum stearate or even propylene glycol or fatty acid esters. When propylene glycol is used, the propylene glycol also can in many instances cause allergic or contact dermatitis. In this case, the anti-dermatitic agent acts against such causation of contact or allergic dermatitis. Solid carriers include silicone, acrylic adhesive, plasticized polyvinyl chloride and the like. By "drug reservoir composition" is meant a pharmacologically active agent taken alone or taken in conjunction with an anti-dermatitic agent in one of the aforementioned carriers.

Membrane 115a, a microporous membrane, may be of any porous material permitting the passage of the pharmacologically active agent and the anti-dermatitic agent and is inclusive of microporous polypropylene, microporous nylon, microporous polycarbonate and the like. The membrane layer may be a single layer or may be of multiple layers of selected microporous materials which have been laminated together. The pharmacologically active agent taken further together with the anti-dermatitic agent passes through the micropores which are filled with mineral oil or other carrier material during the fabrication. The control effected by the membrane is not by the dissolution of the drug in the membrane material but merely in travel through the pores.

Membrane 115b, a diffusion controlling membrane, may be of materials in which the pharmacologically active agent dissolves and is inclusive of silicone, ethylene vinyl acetate and polyurethane.

When the rate controlling member is an adhesive rate controlling member 115c, the preferred adhesive is selected from a class of rubber based adhesives. Other adhesives include suitable medical grade adhesives which permit migration. Examples of such adhesives include polymers of esters with acrylic acid, copolymers of the esters with other acrylic derivatives, such as acrylic acids, acrylamides, elastomeric silicone polymers, vinyl polymers, such as polyvinyl alcohols, polyvinylpyrrolidones, polyvinyl acetates, blends of cellulose derivatives and natural gums, such as guar gum, pectin and the like. When the adhesive is to be employed solely as attachment means for a patch, an adhesive having no rate-controlling properties is employed. Generally, such adhesives are acrylate based adhesive systems.

The rate of travel of the pharmacologically active agent taken further together with anti-dermatitic agent is controlled by several factors, the porosity or diffusion coefficient of the pharmacologically active agent in the membrane, the porosity or diffusion coefficient of the anti-dermatitic agent in the membrane, the thickness of the membrane or the rate controlling adhesive, the concentration of the anti-dermatitic agent in the adhesive and the solubility of the pharmacologically active agent as well as the anti-dermatitic agent in the carrier material of the drug reservoir.

Referring to FIG. 10A, which is a cross-sectional view of a medical bandage useful in the practice of our invention, the bandage 210 comprises a backing member 211 that defines the top of bandage 210. Backing member 211 serves as a protective cover for bandage 210 and it imparts structural support to the bandage and it substantially keeps components, e.g., anti-dermatitic agent and pharmacologically active agent in bandage 210 from escaping the bandage. Backing member 211 is made from a material 212 that is substantially impermeable to the components in bandage 210 or member 211 is made from a combination of materials, such as a composite or a laminate to yield a backing member that is substantially impermeable to the passage of components in bandage 210.

A reservoir 213 containing anti-dermatitic agent and pharmacologically active agent adjacent to backing member 211 is positioned immediately below and in contact with one surface 214 of backing member 211. Reservoir 213 bears on its surface distant from backing member 211 a membrane 216 for controlling the release of pharmacologically active agent and anti-dermatitic agent 217 represented by dots from medical bandage 210. In the bandage outer edges 218 of backing member 211 will overlay edges 219 of reservoir 213 and they will be joined along these parameters in a fluid tight arrangement. This sealed reservoir is effected by pressure, fusion, adhesion or through an adhesive applied to the edges of the membrane. In this structure reservoir 213 is contained wholly between backing member 211 and release rate controlling membrane 216 and reservoir 213 does not in this manufacture have any exposed surfaces. In a preferred embodiment, backing member 211 and release rate controlling membrane 216 will be inherently sealable to each other or they will include a sealing means such as a film position between and sealable to both the backing member and the release rate conrolling membrane or by a layer of adhesive. Reservoir 213 comprises a continuous phase as represented by wavy line 221 and it is formed of a fluid to viscous material permeable to the passage of the anti-dermatitic and pharmacologically active agent composition 217. Reservoir 213 also contains a rheological agent 222 represented by dashes. Reservoir 213 contains a dosage unit amount of pharmacologically active agent 217 that is supplied to release rate controlling membrane 216 throughout the medical history of bandage 210. The dosage amount comprises a supply of pharmacologically active agent for one hour, for eight hours for a normal night sleep, for twenty-four hours applied once daily, for forty-eight hours or longer together with an appropriate amount of anti-dermatitic agent to last as long as the supply of pharmacologically active agent lasts. In practicing the therapeutic method of drug administration, a single bandage can be on the skin, more than one medical bandage can be on the skin and the medical bandage can be applied topically successively for the intended result.

Rate controlling membrane 216 has one surface in contact with reservoir 213. Membrane 216, adjacent to reservoir 213, is formed of a material that is dense or microporous and it is a polymeric material that controls the rate of pharmacologically active agent/anti-dermatitic release from reservoir 213. Membrane 216 permits the passage of pharmacologically active agent/anti-dermatitic agent 217 at a rate dependent on the solubility of pharmacologically active agent and anti-dermatitic agent therein as well as on the thickness of the membrane. The dosage rate per area of medical bandage 210, or the flux of pharmacologically active agent/anti-dermatitic agent thus is controlled to the exterior of the bandage by regulating the composition, thickness of membrane 216 and the diffusion coefficient of the anti-dermatitic agent and the diffusion coefficient of the pharmacologically active agent. Medical bandage 210 can be provided with the same surface area and having different dosage of pharmacologically active agent/anti-dermatitic agent release by varying the characteristics of membrane 216. Diffusion coefficients can be determined by standard techniques.

Medical bandage 210 further comprises a layer or lamina of an adhesive 223 in contact with the releasing surface of membrane 216, that is, it is directly below and adjacent to membrane 216 or optionally adhesive 223 extends around the outer parameter of membrane 216. Contact adhesive layer 223 is the presently preferred means by which bandage 210 in this particular embodiment is affixed to a warm-blooded animal, mainly to the area of the skin selected for receiving the pharmacologically active agent (together with the anti-dermatitic agent). The composition and the thickness of adhesive layer 223 are such that layer 223 does not constitute a significant permeation barrier to the passage of pharmacologically active agent and anti-dermatitic agent and it should preferably be substantially more permeable to the passage of anti-dermatitic agent and pharmacologically active agent than membrane 216, and it is at least as permeable to pharmacologically active agent and anti-dermatitic agent as membrane 216. The adhesives used for the present purpose are dermatologically acceptable and they permit the bandage to be easily removed from the skin after the period of administration of pharmacologically active agent and anti-dermatitic agent.

Medical bandage 210 may also include a release liner 224 in contact with adhesive layer 223. Release liner 224 protects the bandage and just prior to use, it is pulled away from adhesive layer 223 and discarded. Release liner 224 is made from a material that is substantially impermeable to the passage of anti-dermatitic agent as well as pharmacologically active agent. The same material used for backing member 211 may be used to make release liner 224 provided they are strippable materials and compatible with medical bandage 210. In a preferred embodiment, the release liner is made with a pull tab to facilitate removal of the liner from bandage 210 before use.

Components of the embodiment of our invention as set forth in FIG. 10A are specifically set forth in U.S. Pat. Nos. 4,661,105 issued on Apr. 28, 1987, the specification for which is incorporated by reference herein.

Figure 10B:
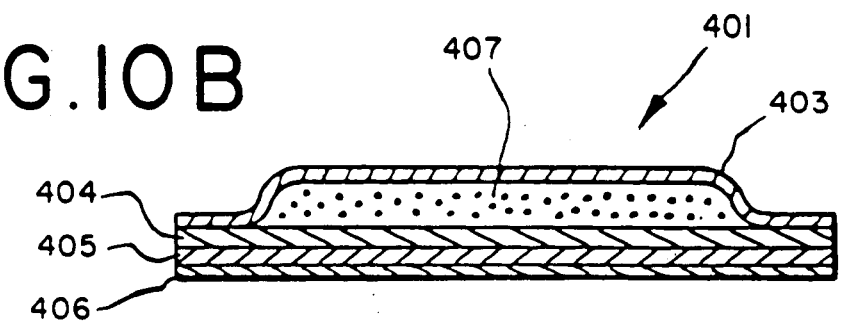
FIG. 10B is a schematic cross-sectional representation of a controlled transdermal nitroglycerin delivery system for delivering nitroglycerin at high transdermal fluxes, and containing at least one of its components an anti-dermatitic agent different in chemical structure from the chemical structure of the pharmacologically active agent.

Referring to FIG. 10B, the system 401 is preferably fabricated in the form of a laminated pouch formed from a impermeable backing 403 bonded at its periphery to and spaced apart at its central portion from a pharmacologically active agent/anti-dermatitic agent release rate controlling membrane 404 which is coated with a contact adhesive 405 provided with a protective removable liner 406 intended to be stripped from the device prior to use. Although the preferred embodiment illustrated herein shows the use of an in-line adhesive 405, other means for holding the system in pharmacologically active agent, anti-dermatitic agent and permeation enhancer transmitting relationships to the skin include circumferentially located adhesives, adhesive overlays, belts, buckles, elastic bands or the like. The pouch is filled with a composition 407 which comprises the pharmacologically active agent, the anti-dermatitic agent and permeation enhancer reservoir preferably in the form of a viscous gel or paste Certain critical interrelationships between the compositions of the membrane 404 and the pharmacologically active agent/anti-dermatitic agent/ enhancer reservoir 407 of the transdermal delivery system must exist according to this invention The specific variables and materials that can be used are set forth in U.S. Pat. No. 4,681,584 issued on July 21, 1987 and U.S. Pat. No. 4,144,317, the specifications for which are incorporated by reference herein.

Figure 11:
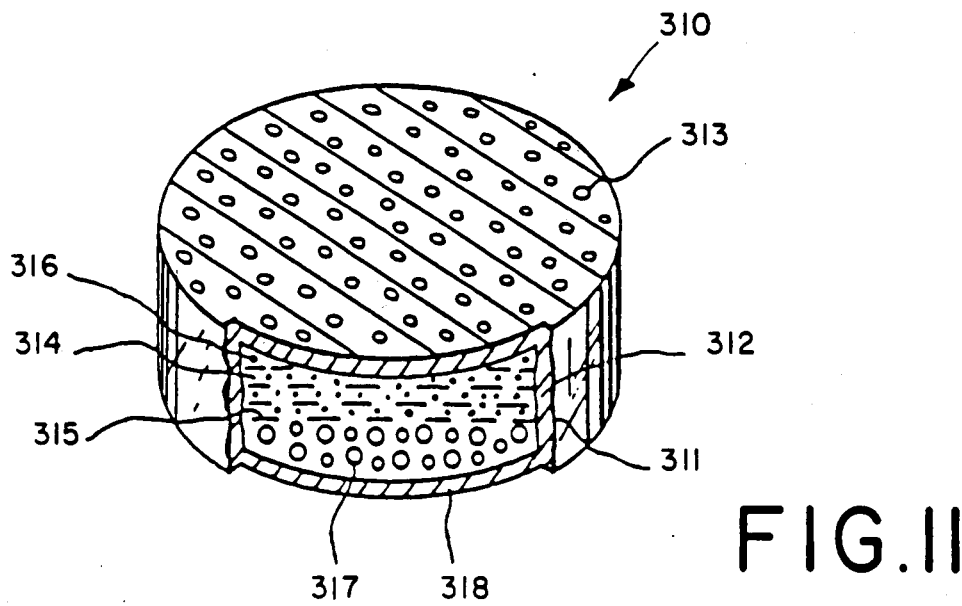
FIG. 11 is an open view of a dispenser designed with means for forming a releasing passageway in operation in a fluid environment of use, containing a pharmacologically active agent in its internal space and admixed therewith an anti-dermatitic agent, the anti-dermatitic agent having a chemical constituency different from the pharmacologically active agent.

FIG. 11 depicts another embodiment of the article of our invention, dispenser 310. FIG. 11 is an open view of dispenser 310. In FIG. 11, dispenser 310 comprises body 311, wall 312, internal compartment 314, thermoresponsive composition 315 containing pharmacologically active agent in admixture with anti-dermatitic agent 316 and osmotically effective solution producing means 317 In FIG. 11, dispenser 310, wall 312 comprises a releasing means 313 formed of a microporous composition. In this embodiment, a section of wall 312 contains a pore forming agent that is removed from wall 312 in the environment of use to form a pore of controlled release dimensions or in another embodiment wall 312 is formed in a part of a microporous composition comprising a plurality of micropores of precontrolled dimensions. In FIG. 11, wall 312 comprises also in at least a part of section 318 formed of a composition permeable to the passage of fluid and substantially impermeable to the passage of osmotically effective compound 317. In FIG. 11, thermo-responsive composition 315 containing pharmacologically active agent/ anti-dermatitic agent formulation 316 is immediately adjacent to the interior surface of microporous releasing means 313 for its passage through the pores. Microporous pharmacologically active agent/anti-dermatitic agent releasing surface is an additional dispensing advantage provided by this aspect of the invention, as it functions like a diffuser for diffusing the agent over a larger agent receiving surface. This action of presenting the agent over a broad tissue area lessens the incidence of tissue irritation associated with tissue irritating agents; and the incidence of such irritation is substantially dispensed with now by the additional use of the anti-dermatitic agent as exemplified in Example I, infra.

Figure 13:
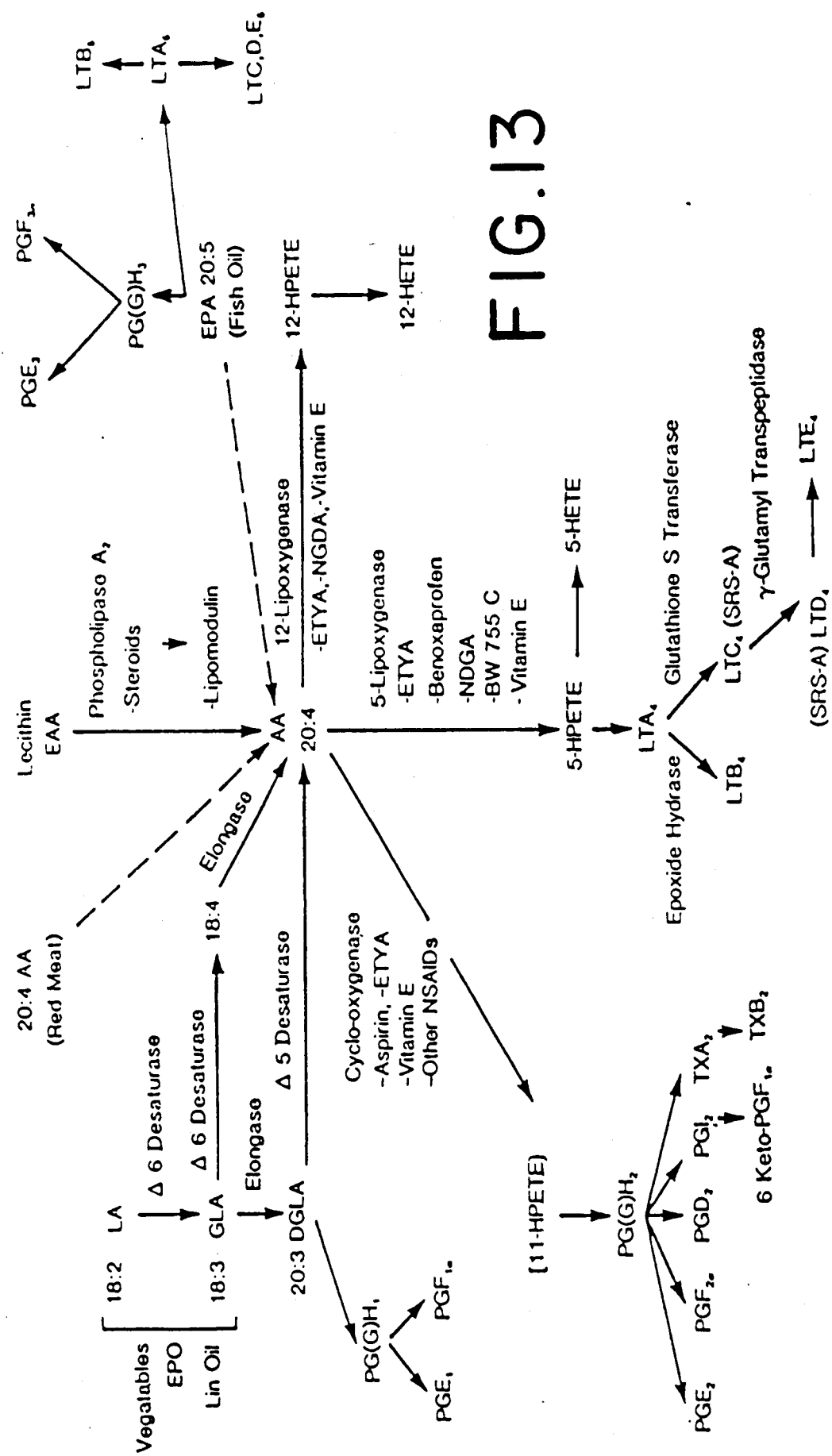
FIG. 13 is a schematic diagram of an arachidonic acid transformation cascade.

Referring to FIG. 13, the arachidonic acid (AA) transformation cascade. Two dashed lines indicate dietary sources of AA or dietary supplements (EPA) that can compete with AA for transformation. EPO indicates evening primrose oil; LIN Oil, linseed oil; LA, linoleic acid; GLA, gamma-linolenic acid; DGLA, dihomo gamma-linolenic acid; PG, prostaglandin; HPETE, hydroperoxyeicosatetraenoic acid; HETE, hydroxyeicosatetraenoic acid; EAA, esterified arachidonic acid; EPA, eicosapentaenoic acid; LT, leukotriene; ETYA, eicosatetraynoic acid; TX, thromboxane; NSAID, nonsteroidal anti-inflammatory drug; NDGA, nordihydroguaiaretic acid; BW, Burroughs Wellcome; SRS, slow-reacting substance, Numerals (e.g. 20:3) indicate number of carbon atoms to left of colon and number of double bonds (i.e., degree of unsaturation) to right of colon.

The substance of this figure is more fully described in Arch. Dermatol, Vol. 119, July, 1983 at page 541 entitled "Editorial/Leukotrienes and Other Lipoxygenase Products in the Pathogenesis and Therapy of Psoriasis and Other Dermatoses" incorporated by reference herein.

Figure 14:
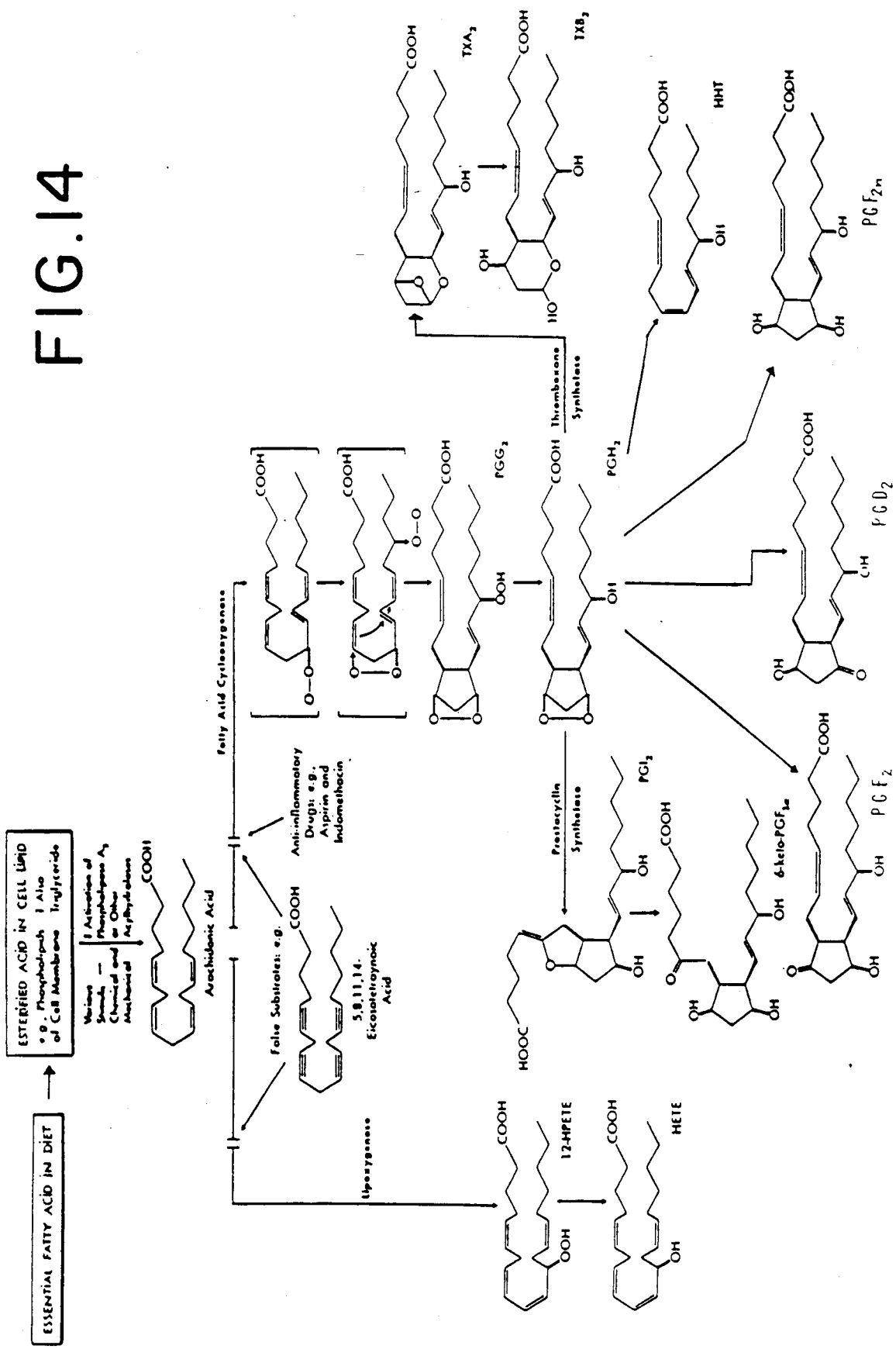
FIG. 14 is a schematic diagram showing biosynthesis of the products of arachidonic acid.

FIG. 14 is a diagram setting forth biosynthesis of the products of arachidonic acid. Two major routes of metabolism of arachidonic acid are shown. The lipoxygenase pathway leads to HPETE and HETE; the cyclooxygenase pathway leads to the cyclic endoperoxides (PGG and PGH) and the subsequent metabolic products. Compounds such as aspirin and indomethacin inhibit the cyclooxygenase while 5,8,11,14-eicosatetraenoic acid inhibits both pathways. The biosynthesis is more fully described in Chapter 28, "Prostaglandins, Prostacyclin, and Thromboxane A" by Salvador Moncada, Roderick J. Flower and John R. Vane in the text entitled "The Pharmacological Basis of Therapeutics" 7th Edition (Goodman and Gilman's), published by the McMillin Publishing Company, 1985, incorporated by reference herein.

EXAMPLE I

In the example, the following definitions apply:
Ro 22-1327 is the compound having the structure:

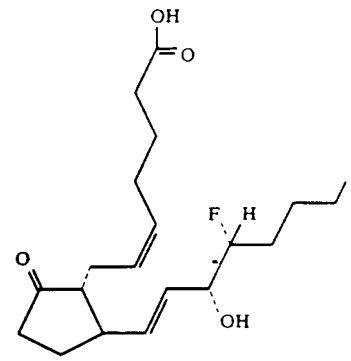

also called (5Z, 13E, 15R, 16R)-16-fluoro-15-hydroxy-9-osoprosta-5-dienoic acid.

Fluocinonide is the compound having the structure:

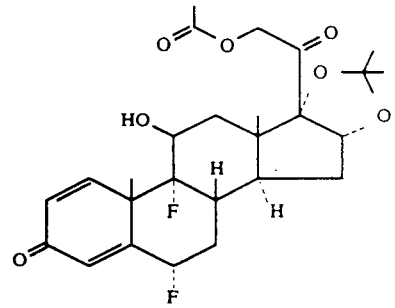

Guanfacine is the compound having the structure:

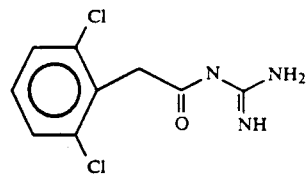

Clonidine is the compound having the structure:

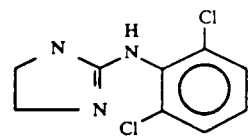

Mirataine BB is the compound having the structure:

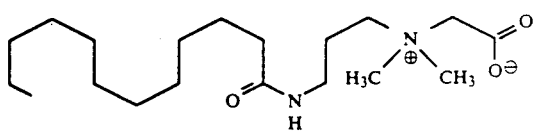

Figure 12:
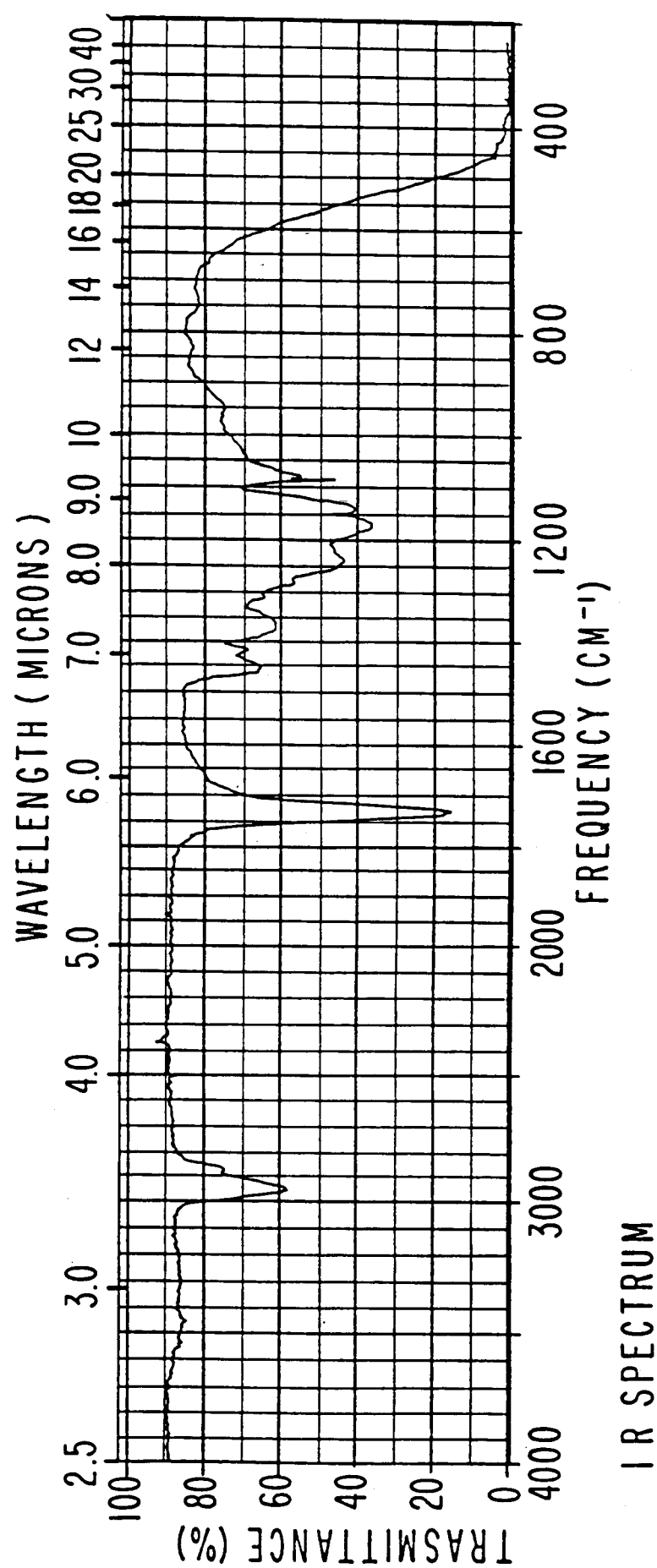
FIG. 12 is the infra-red spectrum of ADMEX ® 760 as used in Example I, infra.

ADMEX® 760 is a high molecular weight (8,000) adipate plasticizer manufactured by Sherex of Nuodex, Inc. having an infra-red spectrum as set forth in FIG. 12.

Hydrocortisone is the compound having the structure:

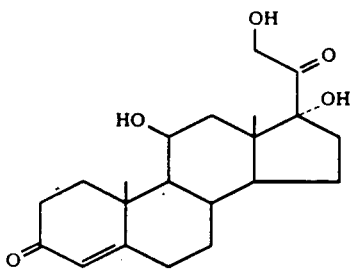

Guanfacine Hydrochloride is the compound having the structure:

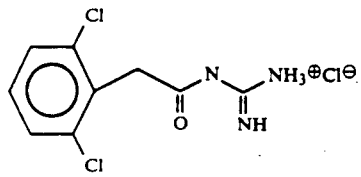

Hexylene Glycol is the compound having the structure:

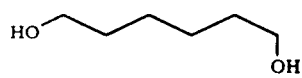

Fluphenazine is the compound having the structure:

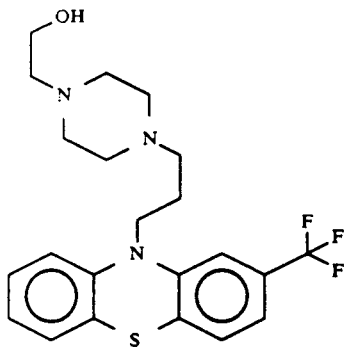

"Macule" is a well-demarcated alteration in the color of the skin without elevation or depression.

"Papule" is a well-demarcated, solid elevation of the skin with no clearly discernible visible fluid.

The Grading System for this example is as follows:
±/−. . . faint, or spotty, pink color within test site;
1. . . uniform pink color covering all of test site;
2. . . uniform pink to red color covering all of test site;
3. . . bright red color covering all of test site;
4. . . uniform bright red color covering all of test site with edema, blisters, or weeping.

EXAMPLE I (a)

PROTOCOL—Ro 22-1327

Objective—To block the contact dermatitis observed following application of Ro 22-1327 patches to the skin through the incorporation of fluocinonide in the patch.

Materials—One formulation of the antihypertensive drug Ro 22-1327 was used, in which either 0%, 0.1%, 1.0% or 5% fluocinonide was incorporated.

Methods—Four patches containing Ro 22-1327 and fluocinonide at either 0%, 0.1%, 1.0%, or 5.0% were applied to the upper arms (two per arm) of a single human subject. The patches were removed at 8 hours and the sites observed for signs of dermatitis immediately and 16 hours later.

In a second test, one Ro 22-1327 patch containing 1.0% fluocinonide was applied to the upper arm of a single human subject and removed after 24 hours. The site was examined immediately for signs of dermatitis.

Results—The incorporation of 1.0% fluocinonide into the Ro 22-1327 patch resulted in a significant reduction in the erythema associated with the use of Ro 22-1327.

Contact Dermatitis to Ro 22-1327

| | Test 1 | |
|---|---|---|
| Fluocinonide Concentration | 8 Hour Reading | 24 Hour Reading |
| 0 | 3 + erythema* | 2 + erythema |
| 0.1% | 3 + erythema* | 1 + erythema |
| 0.1% | trace erythema | 0 |
| 5.0% | 1 + erythema | trace erythema |

| | Test 2 |
|---|---|
| Fluocinonide Concentration | 24 Hour Reading |
| 1.0% | erythema limited to area within patch |

*erythema extended outside of patch area.

EXAMPLE I (b)

PROTOCOL—GUANFACINE

Objective—To block the contact dermatitis observed following application of guanfacine patches to the skin through the incorporation of hydrocortisone in the patch.

Materials—Two formulations of the antihypertensive drug guanfacine were used in this study. Into each was incorporated hydrocortisone at either 0.5% or 2.0%. Control patches containing no hydrocortisone were also used.

Thus, the following formulations were prepared:

| | Formulation #L438-18W (Parts by Weight) | Formulation #438-18c3 (Parts by Weight) |
|---|---|---|
| Guanfacine HCl | 29.7 | 29.6 |
| Hexylene Glycol | 7.9 | 13.8 |
| Polyethylene Glycol 400 | 0.0 | 7.9 |
| Mirataine BB | 2.0 | 0.0 |
| Dioctyl Phthalate | 33.6 | 26.1 |
| Vinyl Chloride/Vinyl Acetate Copolymer (Containing 96% repeating units of vinyl chloride and 4% repeating units vinyl acetate) | 23.7 | 21.2 |
| Aerosil | 3.1 | 1.4 |

(To make the 0.5% hydrocortisone formulations, 20 mg hydrocortisone was added to 4 grams of the above formulations. To make the 2.0% hydrocortisone formulations, 80 mg of hydrocortisone was added to 4 grams of the above two formulations.)

Methods—Three patches of each of the two guanfacine formulations containing either 0%, 0.5% or 2.0% hydrocortisone, were applied to the upper arm of a single human subject. The patches were removed after 23 hours and the sites observed for signs of dermatitis. One week later, the sites were again observed.

Results—The results are given in the accompanying table. Signs of dermatitis were observed at both the 23 hour and 1 week observation period when no hydrocortisone was incorporated into the patch. No adverse reactions were seen with the 2.0% hydrocortisone patches and the results were variable with 0.5% hydrocortisone patches.

Contact Dermatitis to Guanfacine

| IMMEDIATE REACTION (23 HOURS) | | |
|---|---|---|
| Hydrocortisone Concentrations | Formulation #L438-18w | Formulation #L438-18C3 |
| 0% | red macule | red macule |
| .5% | slight redness | no reaction |
| 2.0% | no reaction | no reaction |

| DELAYED REACTION (1 WEEK) | | |
|---|---|---|
| Hydrocortisone Concentration | Formulation # | Formulation # |
| 0% | red papule* | red papule* |
| .5% | red papule* | no reaction |
| 2.0% | no reaction | no reaction |

*edematous (i.e., fluid containing) plaque, almost microvesicular in appearance.

EXAMPLE I (c)

Portocol—Fluphenazine

Objective—To block contact dermatitis observed following application of fluphenazine patches to the skin through incorporation of fluocinonide in the patch.

Materials—One formulation of the anti-psychotic drug fluphenazine was used in which either 0%, 1% or 5% fluocinonide was incorporated.

Methods—Three patches containing fluphenazine and fluocinonide at either 0%, 1% or 5% of fluocinonide were applied to the upper arm of a single human subject. The patches were removed at 48 hours and the sites observed for signs of dermatitis immediately and at 72 and 96 hours.

Results—The incorporation of 1% or 5% fluocinonide almost completely blocked the erythema and blistering caused by fluphenazine.

Thus, the following formulations were prepared:

| | Formulation L-473-9 | Formulation L-473-31(1) | Formulation L-473-31(2) |
|---|---|---|---|
| Fluphenazine | 35 | 35 | 35 |
| ADMEX ® 760 | 30 | 30 | 30 |
| Resin (96% vinyl chloride repeating monomeric units and 4% vinyl acetate repeating monomeric units) | 35 | 34 | 30 |
| Fluocinonide | 0 | 1 | 5 |

The results are as follows:

| Percent Fluocinonide | 48 hours | 72 hours | 96 hours |
|---|---|---|---|
| 0% | 4+ | 4+ | 4+ |
| 1% | +/− | 0 | 0 |
| 5% | 1+ | +/− | +/− |

EXAMPLE I (d)

Protocol—Clonidine

Objective—To block contact dermatitis following application of clonidine patches to the skin through incorporation of fluocinonide in the patches.

Materials—One formulation of the anti-hypertensive drug clonidine was used in which either 0% or 2% fluocinonide was incorporated. A second formulation containing no clonidine was also tested.

Methods—Two patches containing clonidine and either 0% or 2% fluocinonide were applied to the upper back of a single human subject. A third patch containing no clonidine and no fluocinonide was also applied as a placebo. The patches were removed after 7 days and the sites read immediately and on the 8th day as well.

Results—The incorporation of 2% fluocinonide significantly reduced the erythema and blistering caused by clonidine.

Thus, the following formulations were prepared:

| | MO617CL/12 | L477-52B | Placebo L1407CLB/161 |
|---|---|---|---|
| Clonidine | 10% | 10% | 0% |
| ADMEX ® 760 | 70% | 68% | 70% |
| Resin (96% repeating units of vinyl chloride and 4% repeating units of vinyl acetate) | 20% | 20% | 30% |
| Fluocinonide | 0% | 2% | 0% |

The results are as follows:

| Fluocinonide | 7 days | 8 days |
|---|---|---|
| 0% | 4+ | 4+ |
| 2% | 1+ | 1+ |
| Placebo | 0 | 0 |

What is claimed is:

1. An article for the controlled release and delivery to animal tissue of a composition of matter, wherein the article comprises
    (a) a plasticized polyvinyl chloride polymer layer comprising from about 10% by weight up to about 75% by weight of polyvinyl chloride resin and from about 20% by weight up to about 85% by weight of plasticizer;
    (b) at least one pharmacologically active agent which is a causative factor in the occurrence of non-allergic or allergic contact dermatitis, which is chemically compatible with said polymer and is in intimate admixture with said polymer, and which is selected from the group consisting of guanfacine, (5Z, 13E, 15R, 16R)-16-fluoro-15-hydroxy-9-oxo-prosta-5-dienoic acid, fluphenazine, and clonidine, wherein said at least one pharmacologically active agent is present in an amount of from about 0.5% by weight up to about 40% by weight based on said polymer layer; and
    (c) a corticosteroid and at least one anti-dermatitic substance which is chemically compatible with the pharmacologically active agent, which prevents the contact dermatitis from arising or minimizes its severity, and which is selected from the group consisting of chemicals that compete with arachidonic acid biotransformation, free radical scavenger substances, Vitamin E, nordihydroguaiaretic acid, Vitamin D, and leukotriene receptor antagonists, wherein said corticosteroid and said at least one anti-dermatitic substance are present in an amount of from about 0.1% by weight up to about 10% by weight based on said polymer layer when said corticosteroid and said at least one anti-dermatitic substance are present in said polymer layer.

2. The article of claim wherein the corticosteroid is selected from the group consisting of:
   (a) hydrocortisone; and
   (b) fluocinonide.

3. The article of claim 1 wherein a backing layer covers the surface of the polymer layer opposite to the surface of the polymer layer in contact with the animal epidermal tissue whereby said backing layer forms a barrier substantially blocking release of said pharmacologically active agent with or without the excipient therefor or enhancer therefor.

4. The article of claim 1 wherein the polymer layer is a solid polyvinyl chloride layer consisting essentially of from about 20% by weight up to about 70% by weight of a polyvinyl chloride resin; from about 20% by weight up to about 70% by weight of a plasticizer; from about 0.5% by weight up to about 40% by weight of a pharmacologically active agent and from about 0.1% by weight up to about 10% by weight of anti-dermatitic agent.

5. The article of claim 1 wherein the polyvinyl chloride resin is a polyvinyl chloride-polyvinyl acetate copolymer containing a minor proportion of vinyl acetate.

6. The article of claim 1 wherein:
   (i) the corticosteroid is hydrocortisone; and
   (ii) the pharmacologically active substance is guanfacine.

7. The article of claim 1 wherein the pharmacologically active substance is selected from the group consisting of clonidine, (5Z, 13E, 15R, 16R)-16-fluoro-15-hydroxy-9-oxoprosta-5-dienoic acid and fluphenazine and the anti-dermatitic substance is fluocinonide.

8. The article of claim 1 wherein the pharmacologically active agent is intimately admixed with a plasticizing quantity of the compound having the structure:

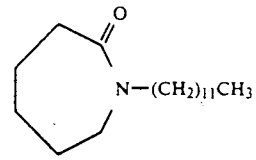

9. The article of claim 1 wherein the pharmacologically active agent and the anti-dermatitic agent are contained in a gel and the gel is contained in a three-space surrounded by an envelope, a major portion of which comprises a lamina consisting essentially of a microporous polymer.

10. An article for the controlled release and delivery to animal tissue of a composition of matter, wherein the article comprises
   (a) a plasticized polyvinyl chloride polymer layer comprising from about 10% by weight up to about 75% by weight of polyvinyl chloride resin and from about 20% by weight up to about 85% by weight of plasticizer;
   (b) at least one pharmacologically active agent which is a causative factor in the occurrence of non-allergic or allergic contact dermatitis, which is chemically compatible with said polymer and is in intimate admixture with said polymer, and which is selected from the group consisting of guanfacine, (5Z, 13E, 15R, 16R)-16-fluoro-15-hydroxy-9-oxoprosta-5-dienoic acid, fluphenazine, and clonidine, wherein said at least one pharmacologically active agent is present in an amount of from about 0.5% by weight up to about 40% by weight based on said polymer layer; and
   (c) a corticosteroid and at least one anti-dermatitic substance which is chemically compatible with the pharmacologically active agent, which prevents the contact dermatitis from arising or minimizes its severity, and which is selected from the group consisting of inhibitor substances of the arachidonic acid cascade, wherein said corticosteroid and said at least one anti-dermatitic substance are present in an amount of from about 0.1% by weight up to about 10% by weight based on said polymer layer when said corticosteroid and said at least one anti-dermatitic substance are present in said polymer layer.

* * * * *